United States Patent
Yeritsyan

(10) Patent No.: US 8,440,593 B2
(45) Date of Patent: May 14, 2013

(54) HERBICIDAL FORMULATIONS FOR TRIETHANOLAMINE SALTS OF GLYPHOSATE

(75) Inventor: Karen Yeritsyan, Dunedin (NZ)

(73) Assignee: Donaghys Industries Limited, Christchurch (NZ)

( * ) Notice: Subject to any disclaimer, the term of this patent is extended or adjusted under 35 U.S.C. 154(b) by 89 days.

(21) Appl. No.: 12/747,620

(22) PCT Filed: Oct. 30, 2008

(86) PCT No.: PCT/NZ2008/000285
§ 371 (c)(1),
(2), (4) Date: Jul. 8, 2010

(87) PCT Pub. No.: WO2009/075588
PCT Pub. Date: Jun. 18, 2009

(65) Prior Publication Data
US 2010/0311591 A1    Dec. 9, 2010

(30) Foreign Application Priority Data

Dec. 13, 2007 (AU) ................................ 2007242910
Dec. 13, 2007 (NZ) ....................................... 564282

(51) Int. Cl.
*A01N 57/00* (2006.01)
*A01N 57/18* (2006.01)

(52) U.S. Cl.
USPC ........................................ 504/127; 504/206

(58) Field of Classification Search .................. 504/127, 504/206
See application file for complete search history.

(56) References Cited

U.S. PATENT DOCUMENTS

| | | |
|---|---|---|
| 3,799,758 A | 3/1974 | Franz |
| 4,405,531 A | 9/1983 | Franz |
| 5,750,468 A | 5/1998 | Wright et al. |
| 6,277,788 B1 | 8/2001 | Wright |
| 6,451,735 B1 | 9/2002 | Ottaway et al. |
| 6,479,434 B1 | 11/2002 | Gillespie et al. |
| 6,544,930 B2 | 4/2003 | Wright |
| 6,881,707 B2 | 4/2005 | Howat et al. |
| 7,135,437 B2 | 11/2006 | Pallas et al. |
| 2006/0194699 A1* | 8/2006 | Moucharafieh et al. ...... 504/206 |
| 2006/0270556 A1* | 11/2006 | Wright et al. ................. 504/165 |
| 2007/0082819 A1* | 4/2007 | Perry et al. .................... 504/136 |
| 2009/0018018 A1 | 1/2009 | Gioia et al. |
| 2009/0062123 A1 | 3/2009 | Quick et al. |
| 2009/0209425 A1* | 8/2009 | Zhu et al. ...................... 504/128 |

* cited by examiner

*Primary Examiner* — Alton Pryor
(74) *Attorney, Agent, or Firm* — Greer, Burns & Crain, Ltd.

(57) ABSTRACT

A high strength herbicidal composition including water; glyphosate, predominantly in the form of a combination of triethanolamine salt and potassium salt in solution in the water in an amount of about 350 grams or greater of acid equivalent per liter of the composition wherein the composition is formulated to include triethanolamine in an amount to form a salt with about 10% or greater, by weight, of total glyphosate and to include potassium in an amount to form a salt with a percentage of total glyphosate so that the combined sum of glyphosate in triethanolamine and potassium salts is more than 50% of total glyphosate; and optionally, one or more surfactants and/or one or more humectants.

24 Claims, 1 Drawing Sheet

HERBICIDAL FORMULATIONS FOR TRIETHANOLAMINE SALTS OF GLYPHOSATE

RELATED APPLICATIONS

This application claims the benefit of New Zealand Patent Application No. 564282 filed 13 Dec. 2007, and Australian Patent Application No. 2007242910 filed 13 Dec. 2007, which are incorporated herein by reference in their entirety.

FIELD OF THE INVENTION

The present invention relates to high strength formulations of glyphosate, incorporating triethanolamine salts of glyphosate, and in particular, formulations comprising the combination of these salts with potassium salts, and methods of use thereof.

BACKGROUND OF THE INVENTION

Glyphosate is a known, effective herbicide. There are several organic ammonium salts of glyphosate useful as herbicides, including the methylamine salt and dimethylamine salt, and, as an example, monoalkylammonium and dialkylammonium (see, e.g., U.S. Pat. No. 4,405,531). Various glyphosate formulations are currently marketed, many of which are aqueous solutions that can be used as is or diluted prior to use.

Typically the glyphosate is provided as a salt that exhibits sufficiently high solubility in water to provide a high strength herbicidal formulation. For example, high strength formulations are known for the isopropylamine salt (IPA), the monoethanolamine (MEA) salt, and various formulations of the potassium (K) salt of glyphosate (see, e.g., U.S. Pat. No. 6,277,788; U.S. Pat. No. 6,365,551; WO 01/89302).

A high strength formulation is desirable for a variety of economic and environmental reasons. For example, it is desirable to provide a high strength formulation to reduce shipping and handling costs and to reduce the amount of packaging material that must be disposed. The high strength formulations are preferably stable and retain potency during storage and shipping. Furthermore, the high strength formulation are optimally provided as a clear, homogeneous liquid that is stable at temperatures at least as high as 50° C. and does not exhibit any precipitation at temperatures as low as 0° C.

However, high strength formulations can result in high viscosity. For example, formulations of the commonly used IPA salt of glyphosate become increasingly viscous at concentrations greater than 350 gram acid equivalent per liter (gae/l), particularly at concentrations greater than 440 gae/l. The high viscosity makes the formulation difficult to measure and pump, especially at the lower temperatures typically encountered at the beginning of the growing season.

The available glyphosate formulations typically include a surfactant. Inclusion of a surfactant can be desirable, as the resulting formulation can exhibit increased herbicidal activity or other improved characteristics. For example, glyphosate formulations are known to include alkylbetaine surfactants in combination with other surfactants (see, e.g., WO 03/067689).

A major limitation of the MEA and K salts of glyphosate is the incompatibility with a wide range of surfactants. In particular, polyoxyethylene alkylamines are only compatible with the MEA salt of glyphosate when the sum of the total average number of carbon atoms plus the average number of oxyethylene groups is equal to or less than 25 (see, e.g., U.S. Pat. No. 6,277,788). Similarly, many common surfactants are not compatible with the glyphosate K salt solution. For example, alkylamine ethoxylate surfactants are only compatible (i.e., allow a homogeneous mixture) when the degree of ethoxylation is no more than about 5, and such surfactants have a higher potential to cause eye irritation.

In addition, certain surfactants can interact with the glyphosate salt to increase the viscosity of the herbicidal formulation. For example, some of the surfactants in the oxyalkylene alkylamine class of compounds, when combined with the glyphosate salt, increase the viscosity of the formulation. If the viscosity is too high, handling of the concentrated herbicide can be difficult. Furthermore, highly viscous liquids are difficult to accurately measure, either for application to the plants or for dilution to a less concentrated spray solution. Depending upon the concentration and specific surfactant, the herbicidal formulation can form a gel, which makes most applications extremely difficult if not impossible to perform.

In light of the above described problems, there is a continuing need for additional improvements in the relevant fields including improved high strength herbicidal formulations that exhibit low viscosity and are suitably efficacious. The present invention addresses these needs and provides a wide variety of benefits and advantages.

SUMMARY OF THE INVENTION

It has now been found that the triethanolamine (TEA) salts of glyphosate can be used in combination with potassium (K) salts of glyphosate to allow the preparation of advantageous high strength liquid herbicide formulations.

The present invention encompasses a high strength herbicidal formulation comprising: (a) water, (b) glyphosate, predominantly in the form of the TEA/K salts, in solution in the water in an amount of greater than about 350 gae/l of the composition, and (c) optionally, at least one surfactant.

In certain aspects, the high strength herbicidal formulation of the invention includes a herbicidally efficacious surfactant. This surfactant can be selected to enhance the herbicidal activity of the formulation and to minimize the viscosity of the high strength formulation, or provide other advantages.

In one aspect, the invention encompasses a high strength herbicidal composition comprising: (a) water, (b) glyphosate, predominantly in the form of a combination of triethanolamine salt and potassium salt, in solution in the water in an amount of about 350 grams or greater of acid equivalent per liter of the composition, wherein the composition is formulated to include triethanolamine in an amount to form a salt with about 10% or greater, by weight, of total glyphosate and to include potassium in an amount to form a salt with a percentage of total glyphosate so that the combined sum of glyphosate in triethanolamine and potassium salts is more than 50% of total glyphosate (c) optionally, at least one surfactant and/or at least one humectant.

In other aspects, the composition is formulated to include triethanolamine to form a salt with about 10 to about 35%, by weight, of total glyphosate, or in an amount to form a salt with about 10 to about 35%, by weight, of total glyphosate, or in an amount to form a salt with about 15%, by weight, of total glyphosate, or in an amount to form a salt with about 25%, by weight, of total glyphosate.

In particular aspects, the potassium salts of the composition are more than 50% of total glyphosate. In still other aspects, the composition is formulated to include potassium to form a salt with about 30 to about 90%, by weight, of total glyphosate, or in an amount to form a salt with about 65 to about 90%, by weight, of total glyphosate, or in an amount to form a salt with about 85%, by weight, of total glyphosate, or in an amount to form a salt with about 75%, by weight, of total glyphosate.

In yet other aspects, the composition is formulated to include greater than about 350 grams of acid equivalent of glyphosate per liter of the composition, or greater than about 400 grams of acid equivalent of glyphosate per liter of the composition, or greater than about 540 grams of acid equivalent of glyphosate per liter of the composition, or greater than about 580 grams of acid equivalent of glyphosate per liter of the composition, or greater than about 600 grams of acid equivalent of glyphosate per liter of composition.

In other aspects, the composition is formulated to include greater than about 540 grams of acid equivalent of glyphosate per liter of the composition, or greater than about 580 grams of acid equivalent of glyphosate per liter of the composition, or greater than about 600 grams of acid equivalent of glyphosate per liter of composition.

In another aspect, the surfactant of the composition is selected from the group consisting of alkyl polyglucosides, ethoxylated propylene oxide, ethylene oxide/propylene oxide block copolymer, and cationic surfactants like quaternary ammonium compounds and tallow alkylamines, used, for example, as built in systems or tank adjuvants. In particular aspects, the surfactant is an alkyl polyglucoside.

In still another aspect, the humectant of the composition is selected from the group consisting of glycerol, sorbitol, and other mono and polyglycols. In particular aspects, the humectant is glycerol.

In yet another aspect, the invention encompasses a method of inhibiting plant growth which comprises applying to the plant a water-diluted composition, or a concentrated or full-strength composition, of any one of the preceding aspects.

Other aspects and embodiments of the invention are described herein below.

BRIEF DESCRIPTION OF THE DRAWINGS

This invention is described with reference to specific embodiments thereof and with reference to the figures.

DETAILED DESCRIPTION OF THE INVENTION

Figure 1A:
FIGS. 1A-1B: Field testing results for Roundup Transorb® 540 (FIG. 1A) and Glyphosate 580 TEA (FIG. 1B) photographed on Day 14, post application (see Examples).
Figure 1B:

As noted above, the most commonly used formulations of high strength glyphosate are IPA and K salts. The main disadvantages of IPA salt formulations are high viscosity of the solution and high flammability of IPA starting material. This creates inconvenience and potential risk during handling and manufacturing.

As an alternative to IPA, TEA can be used as cations source. TEA formulations have very high viscosity, so to address this, the present disclosure demonstrates that a mixed salt can be used.

In particular, the present inventors have discovered highly advantageous formulations of TEA/K salts. For the TEA/K combination, it was found that two particularly advantageous concentration of cations are firstly about 25% TEA and about 75% K and secondly about 15% TEA and about 85% K. Other advantageous formulations include about 18% TEA and about 82% K, about 20% TEA and about 80% K, and about 23% TEA and about 77% K.

As described herein, the percentage of the composition formulated to include potassium salt or triethanolamine salt is defined as the percentage of total glyphosate that will be in salt form with potassium or triethanolamine, respectively.

In certain aspects of the invention, the TEA can be included, for example, in an amount to form a salt with about 10%, about 12%, about 15%, about 18%, about 20%, about 23%, about 25%, about 28%, or about 30% or greater, by weight, of total glyphosate, or about 10% to about 35%, about 15% to about 20%, about 20 to about 25%, about 20% to about 30%, about 25% to about 30%, about 30% to about 35%, or preferably, about 25% to about 30%, by weight, of total glyphosate. In certain aspects, the remainder of glyphosate can be present in predominantly the potassium salt form.

In other aspects, the potassium can be included, for example, in an amount to form a salt with about 30%, about 40%, about 50%, about 60%, about 65%, about 70%, about 75%, about 77%, about 80%, about 82%, about 85%, about 90%, by weight, of total glyphosate, or in an amount to form a salt with about 30% to about 60%, about 60% to about 90%, about 65% to about 90%, about 70% to about 80%, about 70% to about 85%, about 75% to about 85%, about 80% to about 85%, about 80% to about 90%, about 85% to about 90%, by weight, of total glyphosate.

In particular aspects, the combined sum of glyphosate in triethanolamine and potassium salts is more than 50% of total glyphosate, for example, at least about 50%, at least about 55%, at least about 60%, at least about 65%, at least about 70%, at least about 75%, at least about 80%, at least about 85%, at least about 90%, at least about 95%, at least about 98%, or at least about 99%, of total glyphosate, or in an amount of about 50% to about 100%, or about 60% to about 100%, about 70% to about 100%, about 75% to about 100%, about 85% to about 100%, about 90% to about 95%, about 90% to about 98%, or about 95% to about 100% of total glyphosate.

The TEA salts of glyphosate provide certain advantages over other salts that have been commercialized. In particular, the suggested formulations provide safer options for high loaded glyphosate formulation production, produce stable, practically and economically convenient herbicide concentrates, compared to IPA formulations. The suggested formulations also allow higher acid equivalent concentrations than commercially available K salts.

The TEA/K product has good viscosity, stability, and is inherently safer to produce, as compared to other formulations. The disclosed formulation of TEA/K glyphosate has concentration of 580 gae/l, with mixed salts as disclosed herein. Notably, glasshouse and field trials have shown that visible results are much faster in the case of TEA/K mixed formulation, as compared to each of these salt formulations separately. It is postulated that TEA increases the speed of glyphosate uptake into plants.

The faster action of TEA/K mixed salt formulation is clearly advantageous compared to the single salts. Furthermore, the TEA/K salts have a lower molecular weight than the IPA or MEA salts. Thus, at a given salt concentration, the TEA/K salts of glyphosate have a higher glyphosate acid equivalent content than the IPA or MEA salt.

Thus, in one aspect, the present invention is directed to a high strength herbicidal concentrate composition comprising the TEA salt of glyphosate and an efficacious surfactant. More specifically, the present invention provides a high strength herbicidal concentrate composition comprising: (a) water, (b) glyphosate, predominantly in the form of the TEA/K mixed salts, in solution in the water in an amount greater than about 350 gae/l of the composition, and (c) optionally at least one surfactant.

The herbicidal formulation includes the glyphosate salt in an amount sufficient to provide the high strength formulation. In preferred embodiments, the high strength herbicidal formulation includes greater than about 350 gae/l based upon the glyphosate acid equivalent of the glyphosate salt; more preferably, the high strength herbicidal formulation includes greater than about 440 gae/l based upon the glyphosate acid equivalent of the glyphosate salt; most preferably, the high strength herbicidal formulation includes greater than about 480 gae/l based upon the glyphosate acid equivalent of the glyphosate salt.

In certain aspects, the formulation includes, e.g., about 350 gae/l, about 360 gae/l, about 380 gae/l, about 400 gae/l, about 420 gae/l, about 440 gae/l, about 460 gae/l, about 480 gae/l, about 500 gae/l, about 520 gae/l, about 540 gae/l, about 560 gae/l, about 580 gae/l, or about 600 gae/l, about 620 gae/l, about 640 gae/l, or greater, glyphosate, with upper limits based on solubility.

In other aspects, the formulation includes, e.g., about 350 to about 360 gae/l, about 360 to about 380 gae/l, about 380 to about 400 gae/l, about 400 to about 420 gae/l; about 420 to about 440 gae/l, about 440 to about 460 gae/l, about 460 to about 480 gae/l, about 480 to about 500, about 500 to about 520 gae/l, about 520 to about 540 gae/l, about 540 to about 560 gae/l, about 560 to about 580 gae/l, about 580 to about 600 gae/l, about 600 to about 620 gae/l, about 620 to about 640 gae/l, or greater, glyphosate. It can include a range of about 350 gae/l and greater, with upper limits based on solubility.

In preferred aspects, the present invention is directed to a high strength herbicidal formulation that is storage stable at high temperatures. That is, the formulation forms a clear, homogeneous, stable solution that does not exhibit cloudiness under the storage conditions. More preferably, the formulations of the present invention are stable at temperatures greater than or equal to about 50° C.

In addition, the high strength herbicidal formulation should not exhibit separation or precipitation (or crystallization) of any of the components at low temperatures. For example, the high strength formulation remains a clear solution at temperatures below about 10° C., about 8° C., about 6° C., about 4° C., about 2° C., or preferably at temperatures below about 0° C.

The term "predominantly" in the present disclosure means that at least 50 percent, preferably at least 75 percent and more preferably at least 90 percent by weight of the glyphosate, expressed as acid equivalents, is present as the TEA/K salts. The balance can be made up of other salts, such as the IPA salt, provided that the formulation remains a clear, homogeneous liquid that is stable at temperatures at least as high as 50° C. and does not exhibit any precipitation at temperatures as low as 10° C.

For example, the amount can be at least about 50%, about 55%, about 60%, about 65%, about 70%, about 75%, about 80%, about 85%, about 90% or about 95% TEA/K salts, or about 50 to about 55%, about 55% to about 60%, about 60 to about 65%, about 65 to about 70%; about 70 to about 75%, about 75 to about 80%, about 80 to about 85%, about 85 to about 90%, about 90 to about 95%, or preferably about 50 to about 100% TEA/K salts.

The high strength herbicidal formulation can also include a surfactant, for example, in an efficacy-enhancing amount. In preferred embodiments, the surfactant is selected to be compatible in solution with the high concentration of the glyphosate in the herbicidal formulation. By use of the term "compatible" in the present application, it will be understood by those skilled in the art to include within its meaning that the resulting solution does not exhibit a phase separation or precipitation in the formulation that can be initially observed as a cloudiness and which is typically determined at a specified temperature.

Combinations of surfactant and TEA/K salts of glyphosate can be selected to remain compatible in the formulation at high concentration. The resulting aqueous composition can be provided as a high strength herbicidal formulation. The TEA salts of glyphosate are compatible with a wide variety of surfactants. Preferred surfactants are selected from: alkyl polyglucosides, tallow alkylamines, ethoxylated propylene oxide, ethylene oxide/propylene oxide block copolymer based surfactants, and cationic surfactants like quaternary ammonium compounds and tallow alkylamines, separately or as a mixture (e.g., from about 1:1 to about 6:1, or about 1:6 to about 6:1) used, for example, as built in systems or tank adjuvants.

Non-limiting examples of commercially available alkyl polyglucosides include, for example, AGNIQUE™, or AGRIMUL™ surfactants from Cognis Corporation, Cincinnati, Ohio; Atlox surfactants from Uniqema, New Castle, Del. 19720; or AG surfactants from AKZO NOBEL Surface Chemistry, LLC, such as: AGNIQUE PG 8105 Surfactant—an alkyl polyglucoside in which the alkyl group contains 8 to 10 carbon atoms and having an average degree of polymerization of 1.5; AGNIQUE PG 8166 Surfactant—an alkyl polyglucoside in which the alkyl group contains 8 to 16 carbon atoms and having an average degree of polymerization of 1.6; AGNIQUE PG 266 Surfactant—an alkyl polyglucoside in which the alkyl group contains 12 to 16 carbon atoms and having an average degree of polymerization of 1.6; AGNIQUE PG 9116 Surfactant—an alkyl polyglucoside in which the alkyl group contains 9 to 11 carbon atoms and having an average degree of polymerization of 1.6; AGNIQUE PG 264-U Surfactant—an alkyl polyglucoside in which the alkyl group contains 12 to 16 carbon atoms and having an average degree of polymerization of 1.4; AGNIQUE PG 8107 Surfactant—a $C_{8-16}$ alkyl polyglucoside in which the alkyl group contains 8 to 10 carbon atoms and having an average degree of polymerization of 1.7; AGNIQUE PG 266 Surfactant—a $C_{12-16}$ alkyl polyglucoside in which the alkyl group contains 12 to 16 carbon atoms and having an average degree of polymerization of 1.6; AL 2575/AL 535 Surfactant—a $C_{8-11}$ alkyl polyglucoside in which the alkyl group contains 8 to 11 carbon atoms and having a HLB 12-13; Akzo Nobel AG 6202, AG 6206, or AG 6210 surfactants which are 2 ethylhexyl branched $C_8$; linear hexyl $C_6$; and linear $C_8$-$C_{10}$ alkyl polyglucosides respectively. The alkyl polyglucosides may be present in the formulations of the invention in an amount of about 6 to about 12 percent by weight, based on the total weight of the composition.

In other aspects, the formulations for use in the present invention can be selected to include one or more of the following types of surfactants: alkoxylated alkylamine surfactants having 8 to 22 carbon atoms and a total of 1-20 alkylene oxide groups, available for example from Akzo Nobel as Ethomeen™ C/15, Ethomeen™ T/15, and Ethomeen™ T/20 respectively; etheramine surfactants, such as Tomah™ E-14-2, Tomah™ E-14-5 and Tomah™ E-17-5 (or equivalents) respectively; quaternary ammonium surfactants, such as Barquat PQ-2, Ethoquad™ C/12, Ethoquad™ 18/12 or Tomah™ Q-14-2; amphoteric surfactants, such as Geronol™ CF/AS 30 from Rhodia or Tego™ Betaine F 50 from Goldschmidt; alkyl polyglucosides such as Akzo Nobel AG 6202 or AG 6210; or anionic ester derivatives of alkyl polyglucosides such as the Eucarol™ AGE surfactants. The surfactant may be present in the formulations of the invention in an amount of about 7 to about 15 percent weight/volume. Amounts of surfactant can be higher or lower depending on whether the surfactant is added as a substantive or auxiliary agent, in accordance with standard practice.

For the invention, preferred surfactants include, but are not limited to non-ionic surfactants such as alkyl polyglucosides (e.g., Lutensol® GD 70, AGNIQUE PG 8107-U, Alkadet® 15, etc.), ethylene oxide/propylene oxide block polymers (e.g., Pluronic® PE and Pluronic® RPE range), cationic surfactants like blends of quaternary ammonium compounds (e.g., Geronol™ CF/AS 30, Barquat™ PQ-2, BARDAC 2180, Synthecol Quad LF, etc.), tallow amine ethoxylates surfactants (e.g., Toximal TA-8, Toximal TA-15 etc.).

The surfactants of the invention can be used separately or as a mixture containing 2-3 components ranging from 5%-95%: Exemplary mixtures include: 1) alkyl polyglucosides:quaternary ammonium compound, mixtures ranging from about 1:9 through to about 9:1; 2) alkyl polyglucoside: tallow amine ethoxylated, mixtures ranging from about 1:1 through to about 9:1; and 3) quaternary ammonium compound:EO/PO block polymer, mixtures ranging from about 8:2 through to about 9.5:0.5.

The surfactant can be included in the herbicidal formulation in a desired concentration. Preferably the desired concentration is sufficient to enhance the herbicidal activity of the resulting formulation over that observed with a comparable herbicidal formulation without the surfactant. More preferably, the herbicidal formulation includes the surfactant in amounts not less then 10 g/l, for example, at least about 10 g/l, about 20 g/l, about 30 g/l, about 40 g/l, about 50 g/l, about 60 g/l, about 70 g/l, about 80 g/l, about 90 g/l, about 100 g/l, about 110 g/l, about 120 g/l, about 130 g/l, about 140 g/l, about 150 g/l, about 160 g/l, about 170 g/l, about 180 g/l, about 190 g/l, about 200 g/l, or about 210 g/l, or for example, about 10 g/l to about 50 g/l, about 50 g/l to about 100 g/l, about 100 g/l to about 150 g/l, or about 150 g/l to about 210 g/l, or for example, between about 20 g/l and about 200 g/l, or between about 100 g/l and about 150 g/l.

Other adjuvants may be included in the formulations of the invention, for example, humectants, in particular, polyols (e.g., glycerol, sorbitol, etc.), as well as viscosity adjusting ingredients (e.g., propylene glycol, diethylene glycol, etc.), and pH adjusting ingredients.

It has been determined that, with selection of a specific surfactant in combination with the TEA/K salts of glyphosate, the characteristics (e.g., viscosity) of the resulting herbicidal formulation can be improved. Most preferred are mixtures of surfactants. For example, alkyl polyglucosides can improve viscosity, i.e., the viscosity of the formulation containing the blend of surfactants is significantly lower than that of formulations containing individual surfactants at the same concentration.

In preferred embodiments, the herbicidal formulation is provided to exhibit a viscosity of less than about 2500 cps, about 2000 cps, about 1000 cps, 500 cps, about 300 cps, about 200 cps, about 150 cps, or preferably less than about 100 cps or about 50 cps at around 25° C. The viscosity of the composition is expected to be no more than 2500 cps, no more than 2000 cps, no more than 1500 cps, or no more than 1000 cps, at temperatures as low as 0° C. Viscosity may be measured using any technique known to those skilled in the art, for example, using a Brookfield Synchro-lectric Model LVT Viscometer. An apparent viscosity can be measured by first stirring the sample with a glass rod for 10 seconds, placing the sample on the instrument, turning the instrument on, and measuring the value after 3 revolutions of the measuring dial. Typically the measurement is made using a #3 spindle rotating at 30 RPMs; however depending upon the viscosity of the sample, different spindles and differing rotational speeds can be utilized, as known by those skilled in the art.

In another aspect, the present invention is directed to a method of inhibiting plant growth with a herbicidal formulation. "Inhibition" of growth as used herein includes preventing, reducing, or stopping plant growth as well as killing plants and/or plant parts. The formulation can be provided as described herein. The formulation can be applied as a post-emergent or pre-emergent herbicide. The formulation can be applied as a highly concentrated solution or preferably can be diluted with water prior to application.

The formulations are preferably applied in an amount sufficient to induce a herbicidal effect. For example, a formulation prepared according the present invention can be applied as an aqueous solution to plants including the plants' leaves, stems, branches, flowers, and/or fruit. The herbicidal formulation can be applied in a herbicidally effective amount sufficient to inhibit plant growth or kill individual plants.

The agricultural compositions prepared according to the present invention are highly effective as herbicide compositions against a variety of weeds. The formulations of the present invention can be used as is or combined with other components including other agriculturally acceptable adjuvants commonly used in formulated agricultural products, such as emulsifiers, penetrants, preservatives, freeze point depressants, antifreezes and evaporation inhibitors, antifoam agents, compatibilizing agents, sequestering agents, pH modifiers (buffers, acids, and bases), neutralizing agents, corrosion inhibitors, dyes, odorants, penetration aids, wetting agents, spreading agents, dispersing agents, thickening agents, pigments and/or dyes, fillers, carriers, colorants including salts such as calcium, magnesium, ammonium, potassium, sodium, and/or iron chlorides, fertilizers such as ammonium sulfate and ammonium nitrate, urea, crop oil, humectants such as polyols and mono glycols (e.g., sorbitol, glycerol, butylene glycol, sorbitol, hexylene glycol, caprylyl glycol, neopentyl glycol, ethylene glycol, propylene glycol, polyethylene glycol), and other biologically and/or agriculturally active components, and the like. The concentrated agricultural formulations can be diluted in water and then applied by conventional means well known to those in the art.

The advantages of the high strength formulations of the invention include at least the following: 1) Manufacturing process incorporates non flammable raw materials, and produces no sharp amine smell in factory; 2) Formulations show compatibility with a wide range of surfactants as compared to potassium only formulations; 3) Formulations allow use of biodegradable surfactants (e.g. alkyl polyglucosides), which are more environmentally friendly compared to amine ethoxylate surfactants used with IPA formulations; 4) Formulations require less packaging and less hazardous material for disposal; 5) Formulations are faster and provide better uptake by plants (e.g., full kill in 10-12 days), requiring fewer surfactants (e.g., stickers) compared to other formulations (e.g., full kill in 2 or more weeks); 6) Formulations show stable viscosity which does not significantly change in a wide range of temperatures, making the formulations easy to handle and transfer even in colder weather. Further advantages of the high strength formulations include easier transportation and storage, and more effective production. More final product is contained in each unit. For example, packaging of 1000 liters of a 36% solution requires fifty 20 liter containers. In contrast, 1000 liters of a 58% solution gives the same quantity of active ingredient, but uses only thirty-one 20 liter containers. This provides clear economic benefits.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

Example 1

TEA/K Salt of Glyphosate at 360 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—30% calc.; potassium—70% calc.

For 1000 liter batch:

| INGREDIENT: | QUANTITY (kg): |
|---|---|
| Glyphosate Acid (95%) | 378.947 |
| TEA | 100.3 |
| Potassium Hydroxide (calculated as 105% with the aim of forming a potassium salt with 70% of total glyphosate) | 92.41 |
| Lutensol GD 70 | 140 |
| Sorbitol | 10 |
| Antifoam C | 1 |
| Water | 100+ to volume |

Example 2

TEA/K Salt of Glyphosate at 400 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—25% calc.; potassium—75% calc.

For 1000 liter batch:

| INGREDIENT: | QUANTITY (kg): |
|---|---|
| Glyphosate Acid (95%) | 421.052 |
| TEA | 92.88 |
| Potassium Hydroxide (calculated as 105% with the aim of forming a potassium salt with 75% of total glyphosate) | 110.01 |
| Barquat P-2 | 100 |
| Lutensol GD 70 | 75 |
| Glycerol | 15 |
| Antifoam C | 1 |
| Water | 100+ to volume |

Example 3

TEA/K Salt of Glyphosate at 450 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—20% calc.; potassium—80% calc.

For 1000 liter batch:

| INGREDIENT: | QUANTITY (kg): |
|---|---|
| Glyphosate Acid (95%) | 473.684 |
| TEA | 83.59 |
| Potassium Hydroxide (calculated as 105% with the aim of forming a potassium salt with 80% of total glyphosate) | 132.02 |
| Eucarol AGE | 20 |
| Barquat PQ-2 | 20 |
| Lutensol GD 70 | 100 |
| Propylene glycol | 50 |
| Water | 100 + to volume |

Example 4

TEA/K Salt of Glyphosate at 540 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—10% calc.; potassium—90% calc.

For 1000 liter batch:

| INGREDIENT: | QUANTITY (kg): |
|---|---|
| Glyphosate Acid (95%) | 568.42 |
| TEA | 50.15 |
| Potassium Hydroxide (calculated as 105% with the aim of forming a potassium salt with 90% of total glyphosate) | 178.22 |
| Alkadet 15 | 140 |
| Antifoam US1520 | 1 |
| Water | 100+ to volume |

Example 5

TEA/K Salt of Glyphosate at 580 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—15% calc.; potassium—85% calc.

For 1000 liter batch:

| INGREDIENT: | QUANTITY (kg): |
|---|---|
| Glyphosate Acid (95%) | 610.53 |
| TEA | 80.8 |
| Potassium Hydroxide (calculated as 105% with the aim of forming a potassium salt with 85% of total glyphosate) | 180.8 |
| Alkadet 15 | 75 |
| Barquat PQ-2 | 80 |
| Antifoam C | 1 |
| Water | 100+ to volume |

Example 6

TEA/K Salt of Glyphosate at 580 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—25% calc.; potassium—75% calc.

For 1000 liter batch:

| INGREDIENT: | QUANTITY (kg): |
|---|---|
| Glyphosate Acid (95%) | 610.53 |
| TEA | 134.675 |
| Potassium Hydroxide (calculated as 105% with the aim of forming a potassium salt with 75% of total glyphosate) | 159.524 |
| AGNIQUE PG-8107 - U | 100 |
| Azko Nobel AG 6202 | 25 |
| Antifoam C | 1 |
| Sorbitol | 15 |
| Water | 100+ to volume |

Example 7

TEA/K Salt of Glyphosate at 600 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—15% calc.; potassium—85% calc.

For 1000 liter batch:

| INGREDIENT: | QUANTITY (kg): |
|---|---|
| Glyphosate Acid (95%) | 631.58 |
| TEA | 83.595 |
| Potassium Hydroxide (calculated as 105% with the aim of forming a potassium salt with 85% of total glyphosate) | 187.02 |
| Lutensol GD 70 | 70 |
| Barquat PQ-2 | 30 |
| Azko Nobel AG 6202 | 20 |
| Antifoam US1520 | 1 |
| Propylene Glycol | 30 |
| Water | 100+ to volume |

Example 8

TEA/K Salt of Glyphosate at 600 gae/L

The vat was loaded with water and half of required amount of glyphosate acid. The calculated quantity of water was added in, and then the TEA was pumped in at low speed. The reaction mixture was allowed to cool down, and the rest of glyphosate acid was added. The potassium hydroxide was then loaded, maintaining a temperature below 50° C. This was allowed to sit until all the glyphosate was dissolved. The physical appearance of the solution was checked. In the case of noticeable cloudiness, some additional potassium hydroxide was added. The rest of the ingredients were added in. This was mixed and brought to volume with water. A sample was submitted for laboratory testing. The concentration of active ingredient was adjusted, if required. The calculated percentages were TEA—10% calc.; potassium—90% calc.

For 1000 liter batch:

| INGREDIENT: | QUANTITY (kg): |
|---|---|
| Glyphosate Acid (95%) | 631.58 |
| TEA | 55.73 |
| Potassium Hydroxide (calculated as 105% with the aim of forming a potassium salt with 90% of total glyphosate) | 198.03 |
| Barquat PQ-2 | 30 |
| Amphoterge K-2 | 10 |
| Agnique 8107 - U | 100 |
| Water | 100+ to volume |

For all of the preceding Examples, additional ingredients, including surfactants, defoamers, and humectants, were put in after reaction mixture cooled down and all ingredients had reacted.

For all of the preceding Examples and Example 9, the formulated products showed excellent stability; pH range: 4.0-5.5; and density range: 1.2-1.5.

Example 9

TEA/K Salt of Glyphosate at 400 gae/L Utilising Potassium Hydrogen Carbonate as a Potassium Source The vat was loaded with water and half of required amount of glyphosate acid. The calculated quantity of water was added in, and then the TEA was pumped in at low speed. The rest of glyphosate acid was added. The potassium hydrogen carbonate was added in at small quantities at a time and at low speed. The mixture was allowed to sit until all the glyphosate was dissolved. The physical appearance of the solution was checked. In the case of noticeable cloudiness, some additional potassium hydrogen carbonate was added. The rest of the ingredients were added in. This was mixed and brought to volume with water. A sample was submitted for laboratory testing. The concentration of active ingredient was adjusted, if required. The calculated percentages were TEA—30% calc.; potassium—70% calc.

For 1000 liter batch:

| INGREDIENT: | QUANTITY (kg): |
|---|---|
| Glyphosate Acid (95%) | 421.052 |
| TEA | 111.456 |
| Potassium Hydrogen Carbonate (calculated as 105% with the aim of forming a potassium salt with 70% of total glyphosate) | 183.216 |
| Alkadet 15 | 140 |
| Antifoam C | 1 |
| Barquat PQ-2 | 20 |
| Water | 100+ to volume |

Example 10

Field Trial of TEA 580 Speed of Kill in Comparison to Roundup Transorb®

Introduction: The purpose of the trial was to measure the Glyphosate 580 TEA (AGNIQUE™ AGNIQUE PG-8107 surfactant) speed of kill compared to Roundup Transorb® 540. The trial was conducted at Owen Chattertons Farm, Maddisons Road near Rolleston. The test crop was ryegrass and clover pasture.

Sprayer Calibration: Spray width 1.5 meter with Donaghys "small plot sprayer"; 2×1.5 m plots=3 Sq Meter; Sprayer Calibration: 150 ml in 3 and half seconds in a 5 meter run.

Rates:

| Product | Rates L/Hec/200 L $H_2O$ |
|---|---|
| 540 | 2.67 |
| 580 | 2.48 |

Rates are based on 1440 g/ha glyphosate active

Time Schedule:

| Action | Date |
|---|---|
| Trial Spray Date: | Day 1 |

First Results: Day 8

Treatments: Following three treatments were applied in duplicate.

| Treatment | ml/7.5 Sqm/ 150 ml water | herbicide ml/ 500 ml water | Surfactant ml | Water ml |
|---|---|---|---|---|
| Control | — | — | — | 500 |
| Roundup Transorb ® 540 | 2.00 | 6.67 | 0.5 | 493 |
| Glyphosate 580 TEA | 1.86 | 6.21 | 0.5 | 494 |

Results: After 7 days of spray treatments, visual observations clearly showed higher degree of yellowness in Glyphosate 580 TEA plots compared to Roundup Transorb® 540. These observations were photographed. SPAD meter (SPAD-502, hand-held chlorophyll meter, Specialty Products Agricultural Division, Minolta Corporation) was used to measure the ryegrass chlorophyll content for the three treatments. Twenty eight ryegrass flag leaves were picked randomly from each treatment (14 leaves from each replication) and the chlorophyll content was measured by SPAD meter. The decrease in chlorophyll content as compared to control plots were related to speed of kill by the herbicides tested. After 7 days of spray, Glyphosate 580 TEA speed of kill was 41% percent greater than Roundup Transorb® 540.

TABLE

| Ryegrass Chlorophyll Meter Readings | |
|---|---|
| Treatment | SPAD Readings |
| Control | 45.85 |
| Roundup Transorb ® 540 | 25.5 |
| Glyphosate 580 TEA | 15.1 |

It was hypothesized that the faster kill speed of Glyphosate 580 TEA was attributable to the presence of nitrogen in amine form in Glyphosate 580 TEA and surfactant properties of TEA. In particular, the nitrogen containing organic compound TEA presents a nitrogen source for weeds, which increases the uptake of salt, and TEA has properties of a surfactant, which also increases uptake. It was concluded that Glyphosate 580 TEA showed excellent performance seven days post spraying based on the quantitative data on enhanced speed of kill/yellowing by Glyphosate 580 TEA as compared to Roundup Transorb®.

All publications and patents mentioned in the above specification are herein incorporated by reference. Any discussion of the publications and patents throughout the specification should in no way be considered as an admission that such constitute prior art, or widely known or common general knowledge in the field.

Where the foregoing description reference has been made to integers having known equivalents thereof, those equivalents are herein incorporated as if individually set forth. Although the invention has been described in connection with specific preferred embodiments, it should be understood that the invention as claimed should not be unduly limited to such specific embodiments. It is appreciated that further modifications may be made to the invention as described herein without departing from the scope of the invention. The invention illustratively described herein may be practiced in the absence of any element or elements, or limitation or limitations, which are not specifically disclosed herein as essential.

In addition, in each instance herein, in embodiments or examples of the present invention, the terms 'comprising', 'including', etc. are to be read expansively without limitation. Thus, unless the context clearly requires otherwise, throughout the description and the claims, the words 'comprise', 'comprising' and the like are to be construed in an, inclusive sense as opposed to an exclusive or exhaustive sense; that is to say in the sense of "including but not limited to".

What is claimed is:

1. A high strength herbicidal composition comprising: (a) water; (b) glyphosate, predominantly in the form of a combination of triethanolamine salt and potassium salt in solution in the water in an amount of about 350 grams or greater of acid equivalent per liter of the composition wherein the composition is formulated to include triethanolamine in an amount to form a salt with about 10% or greater, by weight, of total glyphosate and to include potassium in an amount to form a salt with a percentage of total glyphosate so that the combined sum of glyphosate in triethanolamine and potassium salts is more than 50% of total glyphosate wherein the viscosity of the high strength herbicidal composition is less than or about 2500 cps at around 25° C.

2. The composition of claim 1, wherein the composition is formulated to include triethanolamine in an amount to form a salt with about 10% to about 35% by weight, of total glyphosate and to include potassium in an amount to form a salt with a percentage of total glyphosate so that the combined sum of glyphosate in triethanolamine and potassium salts is more than 50% of total glyphosate.

3. The composition of claim 1, wherein the composition is formulated to include triethanolamine in an amount to form a salt with about 15%, by weight, of total glyphosate and to include potassium in an amount to form a salt with a percentage of total glyphosate so that the combined sum of glyphosate in triethanolamine and potassium salts is more than 50% of total glyphosate.

4. The composition of claim 1, wherein the composition is formulated to include triethanolamine in an amount to form a salt with about 25%, by weight, of total glyphosate and to include potassium in an amount to form a salt with a percentage of total glyphosate so that the combined sum of glyphosate in triethanolamine and potassium salts is more than 50% of total glyphosate.

5. The composition of claim 1, wherein the composition is formulated to include potassium in an amount to form a salt with about 30% to about 90%, by weight, of total glyphosate.

6. The composition of claim 1, wherein the composition is formulated to include potassium in an amount to form a salt with about 65% to about 90% by weight of total glyphosate.

7. The composition of claim 1, wherein the composition is formulated to include potassium in an amount to form a salt with about 85%, by weight, of total glyphosate.

8. The composition of claim 1, wherein the composition is formulated to include potassium in an amount to form a salt with about 75%, by weight, of total glyphosate.

9. The composition of claim 1, which comprises about 540 grams or greater of acid equivalent of glyphosate per liter of the composition.

10. The composition of claim 1, which comprises about 580 grams or greater of acid equivalent of glyphosate per liter of the composition.

11. The composition of claim 1, which comprises about 600 grams or greater of acid equivalent of glyphosate per liter of the composition.

12. The composition of claim 1, further including one or more surfactants and/or one or more humectants.

13. The composition of claim 12, wherein the one or more surfactants are selected from the group consisting of alkyl polyglucosides, tallow alkylamines, ethoxylated propylene oxide, ethylene oxide/propylene oxide block copolymer and quaternary ammonium compounds.

14. The composition of claim 12, wherein the one or more surfactants comprise an alkyl polyglucoside.

15. The composition of claim 12, wherein the one or more surfactants comprise a cationic surfactant.

16. The composition of claim 15, wherein the one or more surfactants comprise a quaternary ammonium compound.

17. The composition of claim 15, wherein the one or more surfactants comprise a tallow alkylamine.

18. The composition of claim 12, wherein the one or more surfactants comprise a mixture of an alkyl polyglucoside and a quaternary ammonium compound.

19. The composition of claim 12, wherein the one or more surfactants comprise a mixture of an alkyl polyglucoside and tallow amine ethoxylated.

20. The composition of claim 12, wherein the one or more surfactants comprise a mixture of an quaternary ammonium compound and ethylene oxide/propylene oxide block polymer.

21. The composition of claim 12, wherein the one or more humectants are selected from the group consisting of glycerol sorbitol, and other mono and polyglycols.

22. The composition of claim 12, wherein the one or more humectants comprise glycerol.

23. A method of inhibiting plant growth which comprises applying to the plant the composition of claim 1.

24. A method of inhibiting plant growth which comprises applying to the plant a water diluted formula of the composition of claim 1.

* * * * *